United States Patent
Haden (10) Patent No.: US 10,450,125 B2
(45) Date of Patent: Oct. 22, 2019

(54) ORAL HYDRATION SYSTEM

(71) Applicant: Jim Haden, Truckee, CA (US)

(72) Inventor: Jim Haden, Truckee, CA (US)

( * ) Notice: Subject to any disclaimer, the term of this patent is extended or adjusted under 35 U.S.C. 154(b) by 0 days.

(21) Appl. No.: 15/575,662

(22) PCT Filed: Jan. 21, 2017

(86) PCT No.: PCT/US2017/014466
§ 371 (c)(1),
(2) Date: Nov. 20, 2017

(87) PCT Pub. No.: WO2017/127766
PCT Pub. Date: Jul. 27, 2017

(65) Prior Publication Data
US 2018/0312326 A1 Nov. 1, 2018

Related U.S. Application Data (60) Provisional application No. 62/282,000, filed on Jan. 22, 2016.

(51) Int. Cl.
*B65D 83/00* (2006.01)
*A61J 15/00* (2006.01)
(Continued)

(52) U.S. Cl.
CPC ........ *B65D 83/0055* (2013.01); *A61J 9/0661* (2015.05); *A61J 15/0011* (2013.01);
(Continued)

(58) Field of Classification Search
CPC .. B65D 83/0055; A61G 7/0503; A61J 9/0661; A61J 9/006; A61J 9/0653;
(Continued)

(56) References Cited

U.S. PATENT DOCUMENTS 2,510,198 A    6/1950   Tesmer
3,003,727 A * 10/1961   Medor .................. A61J 9/0692
                                                        248/104
(Continued)

FOREIGN PATENT DOCUMENTS

GB           2277452     * 11/1994  ........... A61J 9/0661

OTHER PUBLICATIONS

PCT/US2017/014466 International Search Report dated May 24, 2017.

*Primary Examiner* — J C Jacyna
(74) *Attorney, Agent, or Firm* — Wagenknecht IP Law Group, PC (57) ABSTRACT

A hydration system comprising: a fluid reservoir comprising a means for reversibly mounting the hydration system to a structure; a supply tube fluidly coupled to the reservoir at its distal end; a reversibly compressible chamber fluidly coupled to the supply tube; a mouthpiece proximate to or at a proximal end of the collapsible chamber; and at least two valves that regulate the flow of fluid through the hydration system, wherein a distal valve is positioned at a distal end of the chamber or along the supply tube and closes in response to compression of the chamber to reduce backflow of fluid into the reservoir during compression, and a proximal valve is positioned at the mouth piece, biased closed for regulating the delivery of fluid out of the mouthpiece and prevents or reduces air induction into the mouthpiece.

28 Claims, 6 Drawing Sheets

(51) Int. Cl.
  *A61J 9/06* (2006.01)
  *A47G 19/22* (2006.01)
  *A61M 3/02* (2006.01)
  *A61J 11/00* (2006.01)

(52) U.S. Cl.
  CPC ......... *A47G 19/2266* (2013.01); *A61J 11/002* (2013.01); *A61J 2200/76* (2013.01); *A61M 3/022* (2014.02); *A61M 3/0262* (2013.01); *A61M 2209/10* (2013.01); *A61M 2210/0625* (2013.01)

(58) Field of Classification Search
  CPC ................ A61J 15/0011; A61J 15/0092; A61J 19/0638; A61J 19/0692
  See application file for complete search history.

(56) References Cited

U.S. PATENT DOCUMENTS

| | | | |
|---|---|---|---|
| 4,141,524 A | 2/1979 | Corvese, Jr. | |
| 4,838,875 A | 6/1989 | Somor | |
| 4,852,843 A * | 8/1989 | Chandler | B60N 3/103 248/311.2 |
| 5,094,616 A * | 3/1992 | Levenson | A61C 17/043 433/91 |
| 5,249,702 A * | 10/1993 | Topp | A47G 19/2266 215/229 |
| 5,395,322 A * | 3/1995 | Moser | A47G 21/185 215/11.1 |
| 5,484,405 A | 1/1996 | Edstrom, Sr. | |
| 5,601,207 A | 2/1997 | Paczonay | |
| 6,343,716 B1 | 2/2002 | Baudin et al. | |
| 7,207,968 B1 | 4/2007 | Horcinske | |
| 7,730,565 B1 | 6/2010 | Masson | |
| 8,141,728 B1 * | 3/2012 | Dahler | A61J 9/006 215/11.1 |
| 8,328,049 B1 | 12/2012 | Murrieta | |
| 8,740,167 B1 * | 6/2014 | Collins | A01D 75/00 16/437 |
| 8,790,296 B2 | 7/2014 | Makowski et al. | |
| 2002/0092877 A1 | 7/2002 | Bowman | |
| 2002/0115961 A1 | 8/2002 | Writt, Sr. | |
| 2004/0045980 A1 | 3/2004 | Robins | |
| 2004/0056159 A1 | 3/2004 | Schulze | |
| 2004/0079843 A1 * | 4/2004 | Medwed | A61J 9/0661 248/104 |
| 2004/0232375 A1 | 11/2004 | Steckel | |
| 2007/0012733 A1 | 1/2007 | Horito et al. | |
| 2009/0302261 A1 | 12/2009 | Skillern | |
| 2011/0011819 A1 | 1/2011 | Lee | |
| 2013/0037575 A1 | 2/2013 | van der Molen | |
| 2013/0161350 A1 | 6/2013 | Murrieta | |
| 2014/0050816 A1 | 2/2014 | Campbell | |
| 2014/0171795 A1 * | 6/2014 | Eggers | A61B 5/02028 600/432 |

* cited by examiner

ORAL HYDRATION SYSTEM

CROSS REFERENCE TO RELATED APPLICATIONS

This is a U.S. national phase entry under 35 U.S.C. § 371 of PCT/US2017/014466, filed Jan. 21, 2017, now expired, which claims benefit of priority to U.S. patent application No. 62/282,000 filed Jan. 22, 2016, now expired; the content of each is herein incorporated by reference in its entirety.

TECHNICAL FIELD

The invention relates generally to an oral hydration system and more specifically to an oral hydration system that incorporates a pumping mechanism that provides variable flow rates for hydration and can be reversibly mounted to a variety of structures.

BACKGROUND OF THE INVENTION

Hydration is essential for humans to survive and operate at optimal levels. For many reasons such as physical exertion, limited mobility and other health factors people can have a hard time staying adequately hydrated. In the healthcare settings dehydration is a constant concern and problem. For severe dehydration and patient immobility, intravenous hydration is generally provided, but due to possible infection and patient discomfort it is desirable to avoid if possible but at least transition to oral hydration as soon as possible. Dehydration increases the frequency and severity of many common health issues ranging from diabetes and heart disease to pressure ulcers and urinary tract infections to name just a few. People who are older or have suffered from stroke or dementia, have a reduced desire to drink and are particularly vulnerable to dehydration. Furthermore, dehydration has been shown to increase the length of patient stay in hospitals as well an increased mortality rate. Therefore, there remains a great need in the healthcare industry for safer and easier access to oral hydration to promote better health and outcomes for patients and reduce unnecessary spending.

In the medical field a basic pitcher, cup and a straw are generally provided for the patient. A cup and straw however require sufficient mobility and coordination from the patient, often leading to accidental spills and a reduced desire to drink adequate amounts of liquid. In addition, even mobile patients often do not have the energy and motivation required to frequently sit up and reach for their cup and pitcher. To address these deficiencies the patient must rely on help from a caregiver or nurse to fill the cup and even assist them with drinking. The patient is then dependent on the caregiver who is often very busy with other patients. This leads to inadequate hydration for the patient and increased workload for the caregiver. It is also difficult to keep an accurate record of the amount of liquid consumed. In addition a cup and pitcher are exposed to environmental contaminants and therefore there is risk of contaminating the fluid.

Many attempts have been made to improve oral hydration in the healthcare setting yet there remains deficiencies in the designs, there remains concerns related to ease of use for the patient and caregiver, and they can be costly. Previous hydration mounting systems are overly mechanical and very limiting in their adaptation to a variety of structures. Squeeze bulbs with a one-way valve have been utilized to move fluids through a tube for many different reasons. However, squeeze bulbs are hand operated, which can be difficult for a patient to operate. In addition, fluid transfer can be difficult to regulate since squeezing the bulbs often transfers large volumes of fluid. Additionally prior squeeze bulb configurations do not provide the added options for the user to bite down on the mouthpiece to inject fluid or simply draw fluid by sucking. Furthermore, prior squeeze bulbs are not molded as a single piece with a mouthpiece valve and require additional components therein that could become dislodged and become a choking hazard. Thus, adaptation of such systems provides challenges in that they do not provide for the variety of functional needs required by different user groups.

U.S. Pat. No. 8,790,296, entitled, "Patient Hydration System", describes a patient hydration system having a bladder, flexible tube, safety guard handle, and a mouthpiece. The patient can either draw liquid through the flexible tube and mouthpiece, or the bladder can be hung from an IV tree to utilize gravity for delivering liquid to the mouthpiece. Liquid flow is regulated using a bite-valve, where biting opens the valve to permit flow of liquids, and when the bite is released the flow stops. While biting the valve can stop and start the flow of fluid, the rate of flow is dictated largely by the gravitational force exerted on the fluid. Thus, when the valve is open a patient may receive too much liquid too fast creating a choking hazard. Additionally this system is not convenient to disconnect the supply tube and reservoir to refill.

US Publication 2014/0050816, entitled, "Hydration System" describes a patient hydration system with a fluid reservoir connected by a tube and terminating at a valved mouthpiece. Liquid is transferred through the tubing using gravity or suction. The flow of fluid can be regulated using a bite valve or a hand valve biased in the closed position. A removable holder and safety ring is coupled to the tube to facilitate gripping and sanitation with a very similar design to U.S. Pat. No. 8,790,296 B2. A mouthpiece is described as being of sufficient size to stay in the user's mouth to fit behind the lips or teeth of the subject. A supply tube with a bendable quality is described as attaching to a reservoir.

US Publication 20130161350, entitled, "Medical Patient Oral Hydration System" describes an oral hydration system including a hydration water bladder with a holster and rotatable semi rigid boom. A supply tube connects to the reservoir and terminates in a backflow prevention bite valve. This system is overly complicated and limited in its ability to mount to a variety of structures. Additionally, a user must provide enough suction to initially prime a supply tube.

U.S. Pat. No. 5,484,405, entitled, "Drinking Device for Handicapped Persons" describes a reusable hydration system with a fluid source and bendable tube with a mouthpiece that can be positioned near the users mouth for easy access. A mounting bracket and plate support the fluid bottle and provide means for it to be hung from and IV tree. A one-way valve is utilized to maintain fluid in the supply tube.

Hydration systems are also used in outdoor sporting goods; however, their designs suffer from similar deficiencies as the above medical devices. They frequently operate using a bite valve together with suction to deliver liquid from a reservoir. When the user releases pressure on the mouthpiece the valve closes preventing liquid from leaking out. However, for people exercising or on the move, it is often difficult to use a hand to grab the mouthpiece and forego much needed breathing to suck on the mouthpiece to receive fluids.

Therefore, there remains a need for an improved hydration systems that safely and conveniently deliver liquids to individuals or patients in need of hydration.

BRIEF SUMMARY OF THE INVENTION

The invention addresses the above deficiencies and provides related benefits. In particular, it is an object of the invention to provide a more efficient and safe method for an individual to maintain proper hydration. In particular when mobility of the individual or strength is lessened.

In one aspect of the invention an oral hydration system is provided, which includes a fluid reservoir having a bendable mount configured to reversibly mount the oral hydration system to a structure by bending the mount around the structure; a supply tube fluidly coupled to the reservoir at its distal end; and a compressible chamber configured as a squeeze bulb mouthpiece fluidly coupled to a proximal end of the supply tube, wherein the squeeze bulb mouthpiece is molded as a single piece with a proximal face containing a valve that seals the mouthpiece until deformed by the user.

The mount improves user access to the hydration system by permitting the mounting of the hydration system to a variety of structures. In the medical industry the mount is particularly useful for bed rails. In some embodiments, mount is co-molded or bonded to the reservoir. However, in other embodiments the mount is releasably attached to reservoir.

In embodiments where the reservoir includes a lid, the mount can be formed of a shape memory material and joined to the lid. In some embodiments, the mount is co-molded or bonded to the lid. In other embodiments the mount is releasably attached to the lid.

The supply tube is generally bendable or flexible and can be formed any suitable tubing material used in the corresponding art, such as polysiloxanes (silicone) and other polymers used in the medical device industry. Preferably the supply tube is a medical grade tubing. In some embodiments the supply tube has a bendable guidewire that maintains a bent shape that can be adjustably bent to a variety of orientations and released to maintain the orientations. The guidewire permits movement of the supply tube while permitting the supply tube to stay in a desired position upon release. In further embodiments, the guidewire is configured for reversible connection to a brush sized to brush the interior of the mouthpiece and/or supply tube. In some embodiments, the supply tube is reversibly attached to the reservoir, optionally at a lid, a bendable handle forming part of the reservoir, and/or the mount. Attachment may be by way of magnetic attraction between complementary magnets mounted to the corresponding structures.

In a related aspect the invention also provides a hydration system, which includes a fluid reservoir having a means for reversibly mounting the hydration system to a structure; a supply tube fluidly coupled to the reservoir at its distal end; a reversibly compressible chamber fluidly coupled to the supply tube; a mouthpiece proximate to or at a proximal end of the collapsible chamber; and at least two valves that, together with the chamber, regulate the flow of fluid through the hydration system, wherein a distal valve is positioned at a distal end of the chamber or along the supply tube and closes in response to compression of the chamber to reduce backflow of fluid into the reservoir during compression, and a proximal valve is positioned at the mouthpiece and biased in a closed position for regulating the delivery of fluid out of the mouthpiece and prevent air induction upon decompression of the chamber.

The means for mounting the hydration system can be any suitable structure, which includes the bendable mount, two or more mounts, a hook, a detachable loop, or others.

The compressible chamber, together with the valves provides a pumping mechanism to deliver fluid from the reservoir and out from the mouthpiece. In some embodiments, the chamber is configured as a bellows with alternating folds to direct compression of the chamber longitudinally. In other embodiments the chamber is configured to compress radially. The chamber can be configured as a single chamber or can have two or more sub-chambers, which may further retain different volumes of fluid.

The distal valve can be biased in an open position, such that it temporarily closes only when applying a sufficient fluidic pressure distally from a compressing chamber, thereby preventing or reduce backflow while pumping the chamber to deliver fluid from the mouthpiece. In a preferred embodiments, the distal valve is biased closed and opens in response to a vacuum force induced by decompression of a compressed chamber.

The proximal valve is biased closed and opens in response to a positive force applied by sufficient compressing or pumping the compressible chamber or by applying a vacuum force by sucking from the proximal end. In some embodiments, the proximal valve is a bite valve configured to open when biting the mouthpiece. In still further embodiments, the proximal valve is a bite valve that can also be opened by applying sufficient compression or pumping force to the chamber.

In still further embodiments the hydration system can include a third valve positioned between the distal and proximal valves, optionally at the proximal region of the compressible chamber. In some embodiments the third valve is biased in a closed position and is selectively opened during compression of the chamber to deliver fluid proximally. In some embodiments the distal valve and third valve are each biased in a closed position, such that compression of the chamber selectively opens the third valve, and release of the chamber selectively closes the third valve and opens the distal valve to refill the chamber under vacuum.

The hydration system may also be equipped with an inline flow rate control valve positioned distal to the distal valve that regulates a maximum rate of flow independent of compression. In further embodiments, the flow rate control valve has an adjustable selector to select or index the maximum rate of flow through the flow rate valve. The flow rate control valve regulates the time needed for the chamber and mouthpiece to refill with fluid. This provides a user with an initial bolus of fluid and a delay for chamber refilling, thus preventing overconsumption of fluids. Selection of indexing may be by way of a twist valve that opens when twisting the selector in a first direction and closes when twisting in an opposing direction.

The hydration system can also include a safety ring positioned around the mouthpiece to limit entry of the hydration system into a user's mouth that is to receive hydration.

The mouthpiece is generally formed consistent with insertion into the mouth of an individual requiring hydration. The mouthpiece is typically nonrigid and can be formed of pliable polymer, high density foam, silicone, pva, eva, or other suitable materials. The mouthpiece can be integral with the chamber and the chamber reversibly connected to the supply tube, thereby permitting disconnection and reconnection. Such connection can be by way of barbed fittings, luer locks, complementary threads, friction fit or other suitable connection approaches.

In another related aspect, a fluid reservoir with lid is provided, where the reservoir includes a coated bendable mount that maintains a bent shape under pressure exerted by the reservoir when filled with an aqueous solution, wherein a force need to bend the bendable mount is about three to four times the force exerted by the reservoir in the filled state.

Relatedly, a fluid reservoir with lid is also provided, which includes a bendable guidewire that maintains a bent shape without applying a continuous bending force, a supply tube fluidly connected to the reservoir and an adapter configured to accept the guidewire and the supply tube, thereby providing an adjusting mechanism for the supply tube.

In yet another related aspect, a method for hydration is provided, which includes providing one of the embodied hydration systems filled with a hydrating fluid; and opening the proximal valve to deliver fluid to an individual in need of hydration. In some embodiments the proximal valve is a bite valve that is biased closed, and thus the step of opening the proximal valve includes biting the bite valve. In some embodiments the distal valve remains closed while the proximal valve is open. In some embodiments the chamber is compressed or pumped to increase flow of fluid through the opened proximal valve. In some embodiments sufficient compression or pumping opens the proximal valve whether or not undergoing biting. In embodiments where the hydration system has a third valve positioned between the distal and proximal valves, optionally at the proximal region of the compressible chamber, wherein third valve is biased in a closed position, the method can also include opening the third valve by compressing the chamber. Refilling the chamber under vacuum can be by way of releasing a compressed chamber to open the distal valve by vacuum.

BRIEF DESCRIPTION OF THE DRAWINGS

Embodiments of the invention can be better understood with reference to the following drawings, which are part of the specification and represent preferred embodiments. The components in the drawings are not necessarily to scale, emphasis instead being placed upon illustrating the principles of the invention. And, in the drawings, like reference numerals designate corresponding parts throughout the several views.

DETAILED DESCRIPTION OF PREFERRED EMBODIMENTS

For clarity of disclosure, and not by way of limitation, the invention is discussed according to different detailed embodiments; however, the skilled artisan would recognize that features of one embodiment can be combined with other embodiments and is therefore within the intended scope of the invention.

Unless defined otherwise, all technical and scientific terms used herein have the same meaning as is commonly understood by one of ordinary skill in the art to which this invention belongs. If a definition set forth in this document is contrary to or otherwise inconsistent with a well-accepted definition set forth in the art, the definition set forth in this document prevails over a contradictory definition.

The term "proximal" and "proximate" as used herein refers to a position which is nearest to the patient receiving hydration through the mouthpiece. The mouthpiece is proximate to the supply tube, which is proximate to the reservoir since fluid travels from the reservoir, through the supply tube and into the mouthpiece. The term "at a proximal end" as used herein refers to the half or portion closest to the patient.

The term "distal" as used herein refers to a position which is farthest from to the patient receiving hydration through the mouthpiece. The reservoir is distal to the supply line, which is distal to the mouthpiece.

The term "fluidly coupled" or "fluidly connected" as used herein refers to the joining of two structures, each having a lumen through which a fluid may pass. A variety of complementary structures are known in the art to fluidly couple lumens. Among these include luer locks, complementary mating structures, or friction fit connection.

Among the improvements of the oral hydration systems herein, include an improved pumping mechanism, which results in a variable delivery rate under precise control. In particular, the hydration system permits a caregiver to initially prime a supply of liquid which can be later selectively delivered aggressively or passively as needed by a patient even when in a weakened state.

Among the additional improvements of the oral hydration systems herein, include a bendable mount configured to reversibly mount the hydration system to a structure by bending the mount around the structure or bending the mount to form a handle. In particular, the mount facilitates mounting the hydration system to a bed rail or other appropriate structures.

Among the additional improvements of the oral hydration systems herein, include a supply tube operably connected to a bendable guidewire that permits the supply tube to be bent to a desired position then released to function as a boom, thereby permitting adjustable positioning for a variety of patients.

Although the invention has particular benefit for those in the medical industry, such as for the treatment of hydration in human patients, adaptations of the invention are also envisioned for use with sports, gym workout, outdoor activities, driving, pets or anywhere improved access to hydration is desired.

As depicted collectively in FIGS. 1-5E, an exemplary hydration system 10 provides a fluid reservoir 12; a supply tube 14 fluidly coupled to the reservoir 10 at its distal end 14a; a reversibly compressible chamber 16 fluidly coupled to the supply tube 14; a mouthpiece 18 proximate to but preferably forming a proximal end of the collapsible chamber 16; and at least two valves 20a, 20b that regulate the flow of fluid through the hydration system 10, wherein a distal valve 20a is positioned at a distal end 14a of the chamber 14 or along the supply tube 16 and closes in response to compression of the chamber 14 to reduce backflow of fluid into the reservoir 10 during compression, and a proximal valve 20b is positioned generally at the mouth piece 18 for regulating the delivery of fluid out of the mouthpiece 18, wherein the proximal valve 18 is biased closed to prevent leakage but preferably configured to selectively open when the chamber 16 is sufficiently compressed. Preferably, the hydration system 10 also includes a mount 22 for reversibly mounting the hydration system 10 to a structure 100.

Also as shown in FIGS. 1-5E, a variation of the hydration system 10 provides a fluid reservoir 12 having a bendable mount 22 configured to reversibly mount the oral hydration system 10 to a structure 100 by bending the mount 22 around the structure 100; a supply tube 14 fluidly coupled to the reservoir 10 at its distal end 14a; and a compressible chamber 16 configured as a squeeze bulb with integral mouthpiece 18 fluidly coupled to a proximal end 14b of the supply tube 14, wherein the squeeze bulb mouthpiece is molded as a single piece with a proximal face containing a proximal valve 20b that seals the mouthpiece until deformed by the user.

In each of the related aspects, the reservoir 12 provides a housing for maintaining a supply of liquid and therefore may be adapted from other hydration systems or may be improved as demonstrated herein. Examples of suitable reservoirs 12 include, but are not limited to a bottle, a cup, a glass, a pitcher, a box, or a bag. The reservoir 12 can be either rigid or flexible and can be constructed from any suitable material such as glass, polyethylene terephthalate (PET), high-density polyethylene (HDPE), low-density polyethylene (LDPE), poly(vinyl chloride) (PVC), polypropylene, polystyrene, and other opaque or transparent polymers. To this end, the reservoir 12 can be either disposable or reusable depending on the materials used. In some embodiments the reservoir 12 is insulated or has an insulating sleeve, which can be reversibly removable. In some embodiments the reservoir includes a mechanism for temperature change and adjustment. The skilled artisan will appreciate that the reservoir can have volume measurement and time of day indicia and/or can be made of a material or textured so that it can be written on using pens or markers used in the medical field, such as ballpoint pens, felt tip pens, and others.

In medical applications, it may be desirable to have the reservoir 12 prefilled with liquid; however, in some embodiments the reservoir 12 is Tillable or refillable by an outside source. In furtherance of the above, the reservoir 12 can be pre-filled and refillable after use. A refillable reservoir 12 should have at least one opening large enough to be filled with hydrating liquid, which may include one or more of water, electrolyte liquid, juice, melting ice, thickened liquids, bowel prep, vitamins, medicaments, soft foods, or any other suitable oral liquids. A refillable reservoir 12 also provides a convenient mode to administer one or more therapeutic or analytes in that doses may be adjusted depending on volume.

Figure 1:
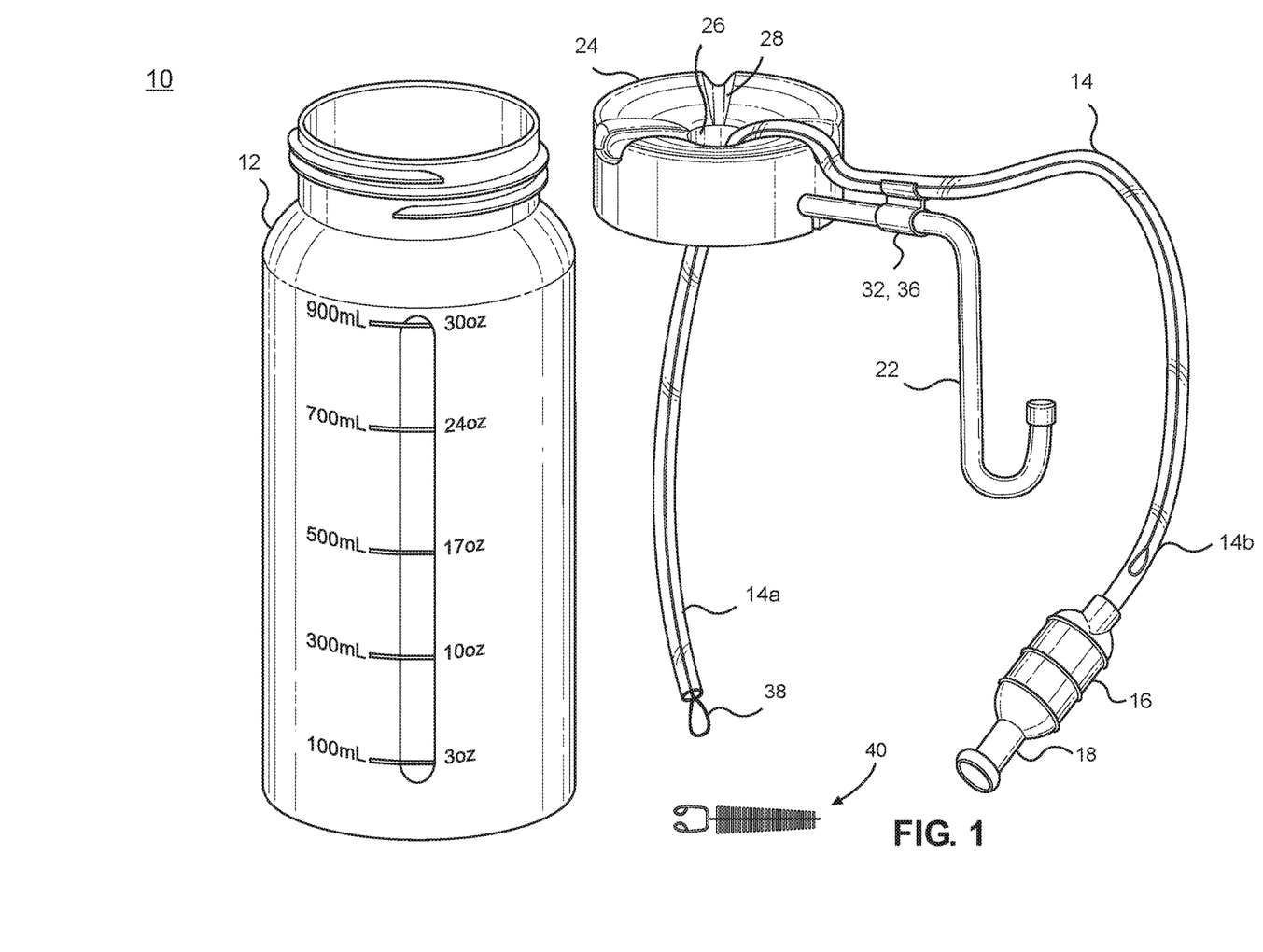
FIG. 1 is a partially exploded view of a preferred oral hydration system 10 equipped with a channeled lid 24.

FIG. 1 depicts a preferred embodiment of the oral hydration system 10 with reservoir 12 having a removable lid 24, which itself has an aperture 26 capable of receiving the supply tube 14 there through and recessed channels 28 that provide one or more guides for guiding or releasably holding the supply tube 14. Another preferred embodiment is depicted in FIG. 2, where a reservoir 12 has a self-supporting opening 30, which provides sufficient rigidity to maintain the integrity of the reservoir 12 when mounted to a structure 100.

Figure 2:
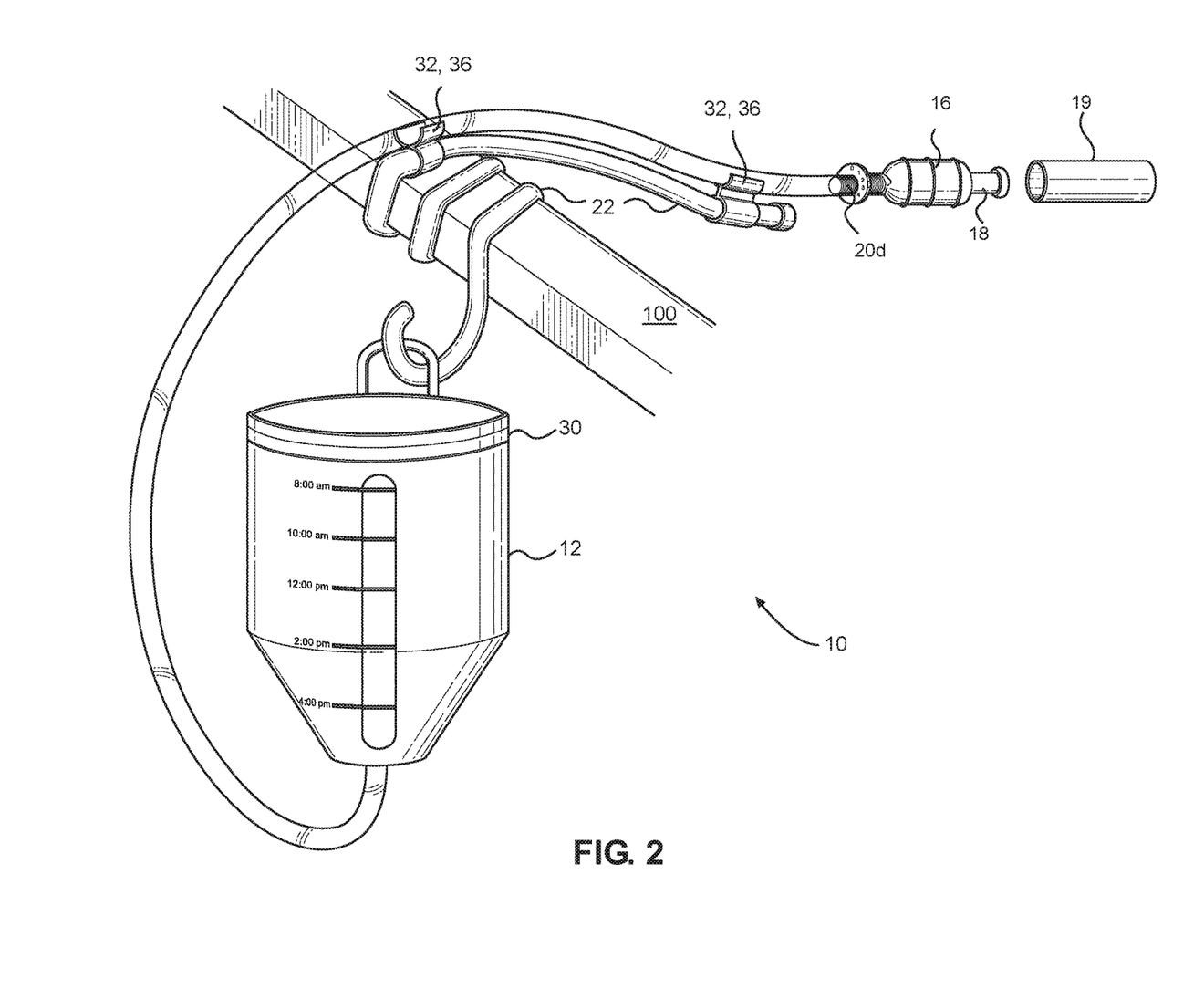
FIG. 2 is another preferred embodiment of the oral hydration system 10 equipped with a self-support opening 30 and a detachable mount 22.

Thus reservoir 12 may be open (as shown in FIG. 2); partially open (as indicated in FIG. 1 due to the gap around the supply tube 14; or sealed fluid tight seal to prevent contaminants from entering the reservoir 12. Furthermore, reservoirs 12 can be include a suitable lid 24 or complementary mating structures (e.g. a ZIPLOC seal). In some embodiments, the reservoir 14 is configured as a collapsible bag and thus collapses as fluid is removed; however, if a rigid or semi rigid reservoir 12 is utilized a one way air vent or other suitable fenestrations or gas permeable barriers can be provided to promote better fluid flow.

Figure 3:
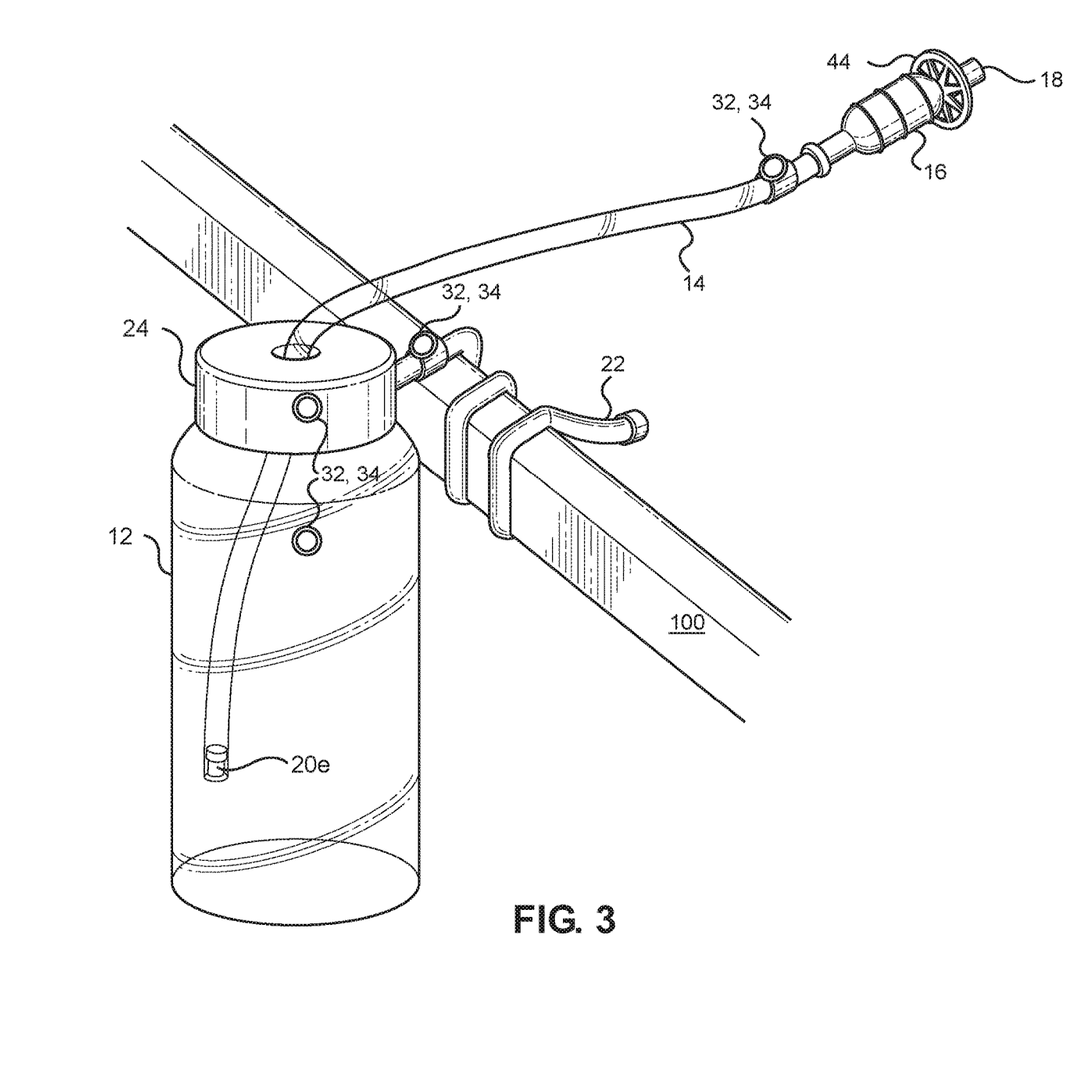
FIG. 3 is another preferred embodiment of the oral hydration system 10 shown mounted to a structure 100 and a boomed supply tube 14.
Figure 4:
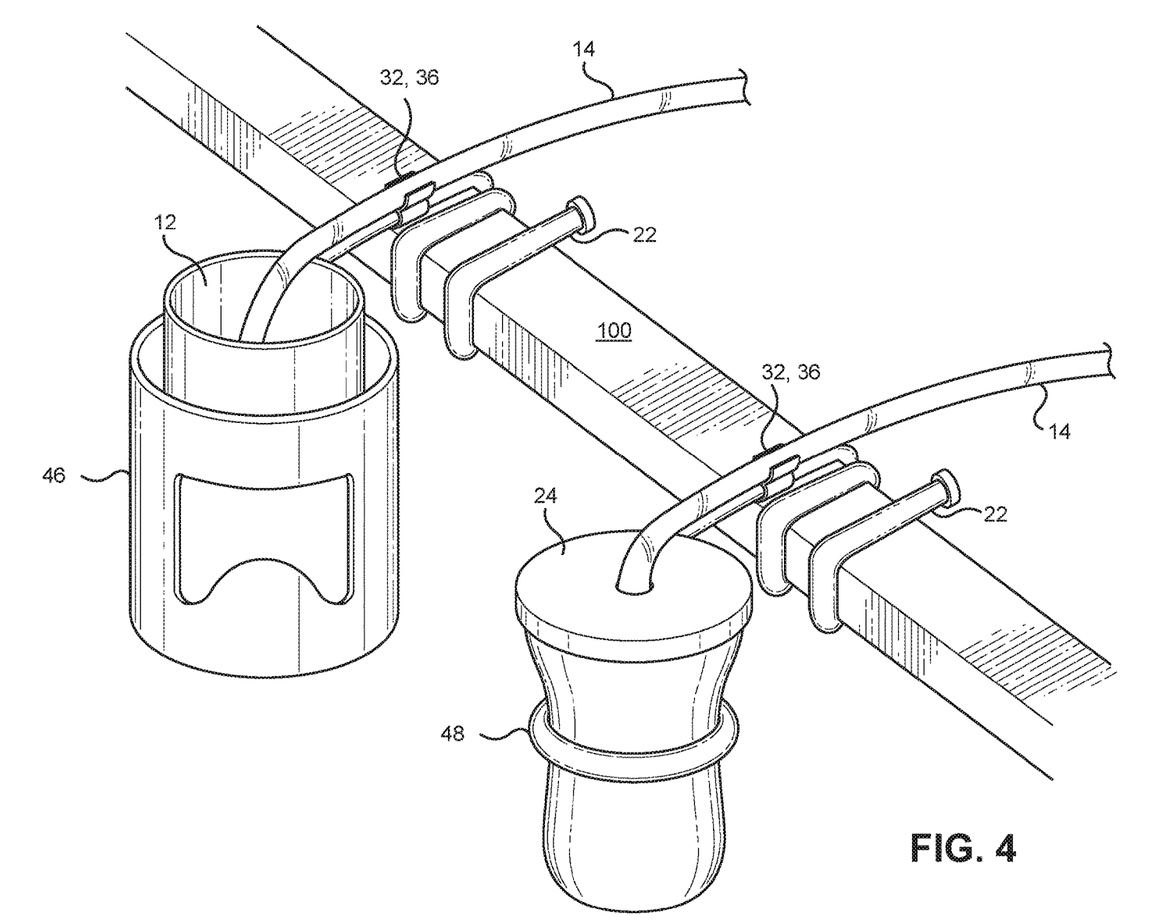
FIG. 4 shows two additional embodiments of the oral hydration system 10 shown mounted to a structure 100.

As shown in FIGS. 2-4, the reservoir 12 can be configured to mount to a variety of structures 100 using a suitable mount 22. Among the structures 100 include an IV pole, a bed, wheelchair, sitting chair, or a walker when the oral hydration system is for medical use. Exemplary mounts 22 can include a reinforced aperture, a hook, a clip, a bendable rod or other hanging structure. In a preferred embodiment the mount 22 is formed as a bendable rod with a polymer coating, such as silicone, that can hook (as shown in FIGS. 1-2) and/or wrap around a structure 100 (as shown in FIGS. 2-4). In some embodiments a bendable mount 22 is formed from a bendable metal or metal alloy coated in a vinyl or silicone. As shown in FIG. 2, in some embodiments, the mount 22 is hooked at one end for hooking to a reservoir 12, is configured for wrapping around a structure 100 to support the reservoir 12, and booms outward to provide a support for the supply tube 14. The supply tube 14 is shown supportively connected to the mount 22 by clips 36. The hooked end of the mount 14 can be pre-formed and more rigid than the remaining portion of the mount 22, but this is not a requirement. In any event, the bendable mount 22 should maintain a sufficiently bent shape under pressure exerted by the reservoir 12 when filled with an aqueous solutions so that the mount 22 does not release the reservoir 12. In a further nonlimiting embodiment a force need to bend the bendable mount 22 is about three or four times the force exerted by the reservoir 12 in the filled state.

In FIG. 1 and FIG. 3, the mount 22 is co-molded or bonded to the reservoir 12; whereas in FIG. 2, the mount 22 is releasably attached to reservoir 12. In still other variations are provided in FIG. 4, where the mount 22 is affixed to a receptacle 46 or wrapped around a contoured region 48 to hold the reservoir 12. Alternatively, or in addition the reservoir 12 can be configured to stand upright by forming a suitable base.

The supply tube 14 supplies fluid, such as hydrating liquid, from the reservoir 12 to a reversibly compressible chamber 16 via a pumping mechanism. The supply tube 14 can be attached permanently to the reservoir 12 in that it does not disconnect and reconnect. Alternatively, the tube 14 can be releasably mated to the reservoir 12 through surface modification, such as barbs, complementary connectors or friction fit. Suitable connectors can be selected from any that are known in the art to which the invention belongs, such as luer locks, bayonet, or tongue and groove connectors. If using a releasable supply tube connection, a leak proof disconnect system can also be utilized akin to a bayonet or septum/Huber needle configuration known in the medical device arts. Alternatively, as shown in FIG. 1, the supply tube 14 can merely feed through an aperture 26 of the lid 24 to access the internal fluid of the reservoir 12. Thus, the supply tube 14 can be fluidly coupled to the reservoir 12 to access liquid from the bottom, the sides, corners, or from the top of the reservoir 12.

The length of the supply tube 14 can vary depending on the position of the oral hydration system 10 in relation to the individual in need of hydration. Accordingly, the hydration system 10 includes further notable advantages. For example, the hydration system 10 can include means for attaching the supply tube to the reservoir 12 and/or to the mount 22. These means for attachment 32 can be formed integral with the reservoir 12 or mount 22 or attach separately. Nonlimiting examples of suitable means for attachment 32 include a hook, hook and loop (VELCRO), a strap, and a stick on. However, a particularly useful embodiment is shown in FIG.

3, where the supply tube 14 and reservoir 12 and/or lid 24 have magnets 34 that attach to one another to provide a holding mechanism for the supply tube 14. In another particularly useful embodiment, FIGS. 1-2 depict clips 36, slidably positioned along the mount 22, that reversibly clip the supply tube 14, thereby permitting the mount 22 to act as a boom for adjusting the position of the supply tube 14.

The supply tube 14 can be semi-rigid and bendable or can be made semi-rigid and bendable using a suitably formed guidewire 38 so that the supply tube 14 can be suspended and directionally boomed toward the user. This improves patient access to the supply tube 14, prevents the user from pulling the supply tube 14 and reservoir 12 too far, and prevents the user from rolling or sitting on the chamber 16 or mouthpiece 18. An elevated and boomed supply tube 14 also minimizes contact with other surfaces and possible contamination. Such a guidewire 38 can be made from any materials that provide enough rigidity to support the supply tube 14 such that it may be temporarily bent and directed or boomed toward the mouth of the user then moved away as desired. Preferably, the supply tube 14 is formed from a bendable polysiloxane (silicone) or other suitable medical grade bendable polymer to permit bending and preferably the guidewire 38 is formed from a bendable metal alloy. This configuration maintains a bent shape when releasing the bending force thereby providing a supply tube 14 that can be adjustably bent and released for positioning in a variety of orientations. The bendable guidewire 38 may be permanently connected to the supply tube 14 or temporarily connected to the supply tube 14, such as by slidable insertion or movement. Still further, as shown in FIG. 1, the oral hydration system 10 may include a brush 40 adapted for reversible connection to either end of the guidewire 38 and sized to brush the interior of the mouthpiece 18, chamber 16 and/or supply tube 14.

The supply tube 14 terminates proximally at the distal end of a reversibly compressible chamber 16, which itself is fluidly coupled to at least two valves 20a, 20b to form a pumping mechanism. The artisan will appreciate the volume of the compressible chamber 16 can vary but when used in medical situations it is usually at least 1 mL but less than 250 mL, more typically the volume is about 25 mL to 50 mL. The chamber 16 is preferably embodied as a squeeze bulb formed from a polymer, such as a polysiloxane (silicone) that is elastic and contoured to form a mouthpiece 18, such that the chamber 16 deforms when squeezing and returns to its original form when squeezing pressure is released. The chamber 16 can compress longitudinally and/or radially. For instance, longitudinal compression can be achieved by incorporating a bellows configuration having alternating folds and squeezing to induce further folding. A bellows configuration provides an advantage in that the actuating the pumping mechanism is primarily by longitudinal compression, which may prevent leakage during accidentally applied radial forces. A radial compressible chamber 16 can be by way of molding the chamber 16 using a pliable plastic or rubber so that it can be squeezed akin to a squeeze bulb. Further, in configurations where radial compression is desired, the chamber 16 can be made of a same material across the entire chamber 16 or may be made with materials that more easily compress about its mid-region, thereby providing relatively stiffer ends and a relatively softer mid region to further direct pumping or compression at the mid-region.

As will follow, the chamber 16 can have a single undivided central volume or can be formed of two sub-chambers 42a, 42b, such as a smaller proximal sub-chamber 42b and a larger distal sub-chamber 42a. This two sub-chamber 42a, 42b configuration may provide additional advantages in that a slow or low volume delivery approach can be employed from the proximal sub-chamber 42b without affecting the larger distal sub-chamber 42a. This approach permits a smaller aliquot of fluid to be easily delivered without spilling by patients with significant impairment.

As shown in FIGS. 5A-E, the pumping mechanism can be formed using at least two valves 20a, 20b, referred to as a distal valve 20a and proximal valve 20b, but preferably includes a third valve 20c between the distal and proximal valves 20a, 20b. The valves 20a-c can be permanently molded or connected to the chamber 16, mouthpiece 18 or supply tube 14. Further, a reservoir valve 20e may be positioned within the supply tube 14 and within the reservoir 12. The chamber 16 can be reinforced at sections having the valves 20a-c to encourage compression at regions between the valves 20a-c. In particular, the chamber 16 can be reinforced at valve regions by increasing the thickness of the chamber 16 at those regions or increasing polymer cross-linking at those regions. Alternatively, molding the valves 20a-c within the chamber 16 would itself increased the rigidity due to the supporting material surrounding the valve 20a-c. The chamber 16 can be molded with the mouthpiece 18 as one unit or as separate pieces then fused or reversibly attached. The mouthpiece 18 may have a slidable cover 19, such as a soft or high density foam or silicone.

In some embodiments the distal end of the chamber 16 (also referred to herein as "an inlet side") is fluidly coupled to the supply tube 14; whereas the proximal end of the chamber 16 (also referred to as "an outlet side") terminates at or with the mouthpiece 18. The chamber 16 is preferably integral with the mouthpiece 18.

Fluidly connected to the distal or inlet side of the chamber 16 is preferably the distal valve 20a. The distal valve 20a may be any suitable valve such as a diaphragm valve, duck bill valve, a ball valve, a flap valve, a louver valve, or any other valve that closes to block or interfere with the flow of fluid distally during compression of the chamber and permits the flow of fluid proximally to refill the chamber by vacuum during release of a compressed chamber. Preferably, compressing the chamber 16 closes the distal valve 20a to forcibly direct liquid proximally from the chamber 16 and decompressing a compressed chamber 16 opens the distal valve 20a to draw liquid into the chamber 16 from the supply line 14 or reservoir 12.

Fluidly connected to the proximal or outlet side of the chamber 16 or mouthpiece 18 is a proximal valve 20b. The proximal valve 20b may be any suitable valve such as a diaphragm valve, a duck bill valve, a ball valve, a flap valve, a louver valve, or any other valve that regulates flow of liquid. Preferably, the proximal valve 20b is biased closed and substantially compressing the chamber 16 opens the proximal valve to eject liquid proximally from the oral hydration system 10. In some embodiments decompressing a compressed chamber 16 closes the proximal valve 20b to form a vacuum that draws liquid into the chamber 16 from the supply line 14.

With reference to FIGS. 5A-E, the following is an advantageous configuration that delivers fluid using two different mechanisms, each with a different delivery volume and rate. Beginning with FIG. 5A, the compressible chamber 16 preferably includes a distal valve 20a positioned distally, a proximal valve 20b positioned proximally and a third valve 20c positioned between the distal and proximal valves 20a, 20b. Furthermore, the proximal and third valves 20a, 20c define a proximal sub-chamber 42b having a comparatively small volume and the distal and third valves 20a, 20c define a distal sub-chamber 42a have a comparatively larger volume.

Figure 5A:
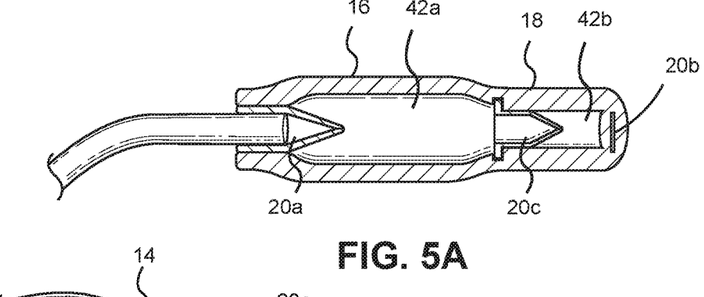
FIGS. 5A-E depict a dual operation of a compressible chamber 16.
Figure 5B:
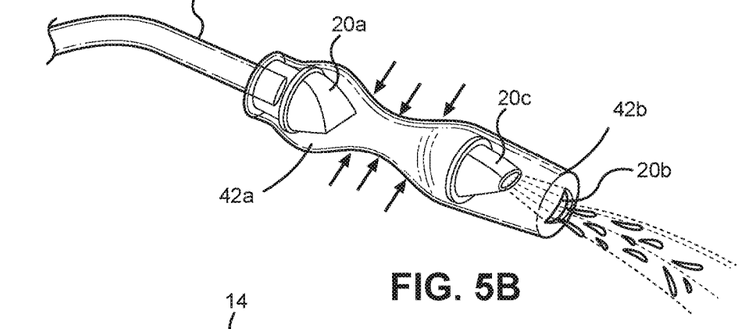

Turning to FIG. 5B, substantial radial compression of the compressible chamber 16 opens the third valve 20c, which is biased closed, to deliver fluid housed in the distal sub-chamber 42a proximally into the proximal sub-chamber 42b and then proximally out of the proximal valve 42b. The distal valve 42a, which is biased closed, remains closed.

Figure 5C:
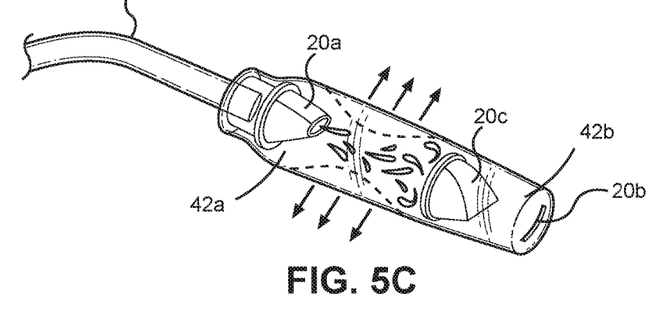

FIG. 5C depicts the decompression of the compressible chamber 16. In particular, release of the compressed chamber 16 induces its expansion and a corresponding vacuum force, which closes the third valve 20c, thereby permitting the proximal valve 20b to return to its biased closed state. The vacuum force opens the distal valve 20a and the resulting vacuum induced through the supply tube 14 draws more fluid into the distal sub-chamber 42a for refilling.

Figure 5D:
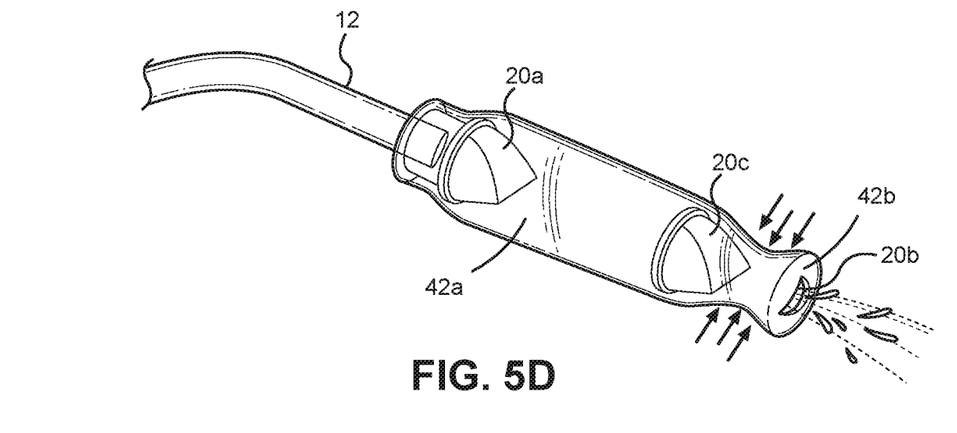
Figure 5E:
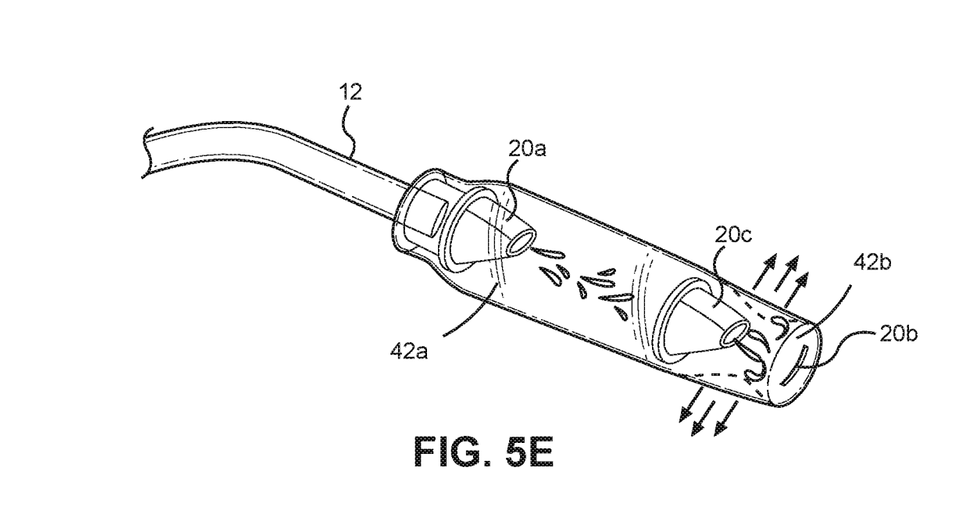

As shown in FIGS. 5D-5E, the smaller proximal chamber 42b can itself be actuated separately to release a smaller volume of fluid, such as for a sip. In FIG. 5D, the proximal sub-chamber 42b is compressed and fluid is expelled from the smaller sub-chamber 42b through the proximal valve 20b. Compressing the proximal sub-chamber 42b can be accomplished by the individual by simply biting the mouthpiece region between the proximal and third valves 20b, 20c. Preferably, the proximal valve 20b is a bite valve and the third valve 20c is a one way valve, such as a flap valve, configured to flow proximally and prevent or minimize the amount of air entering the chamber 16 distally.

FIG. 5E demonstrates the mechanics upon release of the smaller proximal sub-chamber 42b. In particular, releasing the compressing force from the smaller sub-chamber 42b causes its expansion and closure of the proximal valve 20b. Closing the proximal valve 20b induces a vacuum force which opens the third valve 20c to refill the proximal sub-chamber 42b. In some instances the vacuum force is sufficiently strong to also open the distal valve 20a to further refill the emptying distal sub-chamber 42a. Once the vacuum forces are within the tolerances of the biasing forces of the third and distal valves 20c, 20a, they subsequently close Accordingly, among the advantages of the hydration system 10 is the selective delivery of liquid using different approaches, each configured to deliver liquid in different amounts or at different delivery forces. In a first approach, outlined in FIGS. 5A-5C, the compressible chamber 16 is compressed to forcibly inject a greater volume of liquid into the mouth of the user in need of hydration.

In embodiments where the chamber 16 is provided as a bellows configuration with alternating folds (not shown), a user may push the chamber 16 proximally toward their mouth for longitudinal compression along the folds to forcibly eject liquid. In either variation, when a user squeezes the chamber 16 with their fingers, hand, mouth or teeth, the distal valve 20a at the inlet side of the chamber 16 remains closed, which directs liquid flow proximally towards the subject in need of hydration. When the user releases pressure from the chamber 16 it decompresses to about its original volume, which closes the proximal valve 20b and creates a vacuum that opens the distal valve 20a, which pulls liquid from the supply tube 14 into the chamber 16, thereby refilling the chamber 16. Once the vacuum pressure is reduced, the distal valve 20a is permitted to return to its biasing closed state. A benefit of this first approach is that the pumping can be performed either by a subject in need of hydration or a caretaker in instances where the subject is too weak. In addition, by closing the distal valve 20a after refilling the chamber 16, the distal valve 20a helps maintain liquid in the chamber 16 by preventing backflow into the supply tube 14.

In the second approach outlined in FIGS. 5D-5E, the user opens the proximal valve 20b by compression of the proximal sub-chamber 42b. This approach permits the user to receive the liquid at a slow rate and in some embodiments added suction permits opening of the distal valve 20a to receive more liquid from the supply tube 12. A benefit of this approach is that the user can receive the liquid generally at a slower rate or volume than compressing the distal chamber 42a.

In some embodiments the distal sub-chamber 42a and proximal sub-chamber 42b incorporate a same compressing mechanism to inducing pumping; however, in other embodiments each incorporates a different compressing mechanism to induce pumping. For instance, both the distal sub-chamber 42a and proximal sub-chamber 42b can be configured to compress radially to pump fluid. In other embodiments, the distal sub-chamber 42a can be configured to compress primarily radially, while the proximal sub-chamber 42b can be configured as a bellows that compresses primarily longitudinally. In still other embodiments the distal sub-chamber 42a can be configured to compress primarily longitudinally via bellows, while the proximal sub-chamber 42b can be configured to compresses primarily radially.

Referring back to FIGS. 1-5E collectively, the hydration system 10 includes still further advantages. As shown in FIG. 3, in some embodiments, a safety ring 44 is attached to the supply tube 14, mouthpiece 18, or pump chamber 16 to prevent a patient from inserting the hydration system 10 too far and possibly choking. The safety ring 44 can be permanently attached or temporarily attached and removable. The safety ring 44 can be provided with openings so that if a patient inserts the safety ring into their mouth airflow will be maintained. The safety ring 44 can be connected to the supply tube 14 on the proximal side of the pump chamber 16 or between the mouthpiece 18 and chamber 16.

As depicted in FIG. 2, an additional flow rate control valve 20d can be added to the supply tube 14 or inlet side of the chamber 16 to function as a flow restrictor slowing the refill rate of the chamber 16 and the amount of liquid the user can intake over time. This flow rate control valve 20d can provide a fixed amount of liquid flow. The flow rate control valve 20d can also be adjustable and indexed to allow the caregiver and user to set a relative setting and expected flow rate as well provide a complete shutoff. In some embodiments the flow rate control valve 20d has an adjustable selector to select the maximum rate of flow through the flow rate valve 20d. Selection may be by way of a twist valve that opens when twisting the selector in a first direction and closes when twisting in an opposing direction. The flow rate control valve 20d can also be added anywhere along the supply tube 14 as well as a part of the reservoir 12 itself and can take any suitable form as known in the intravenous infusion arts.

As depicted in FIG. 3, a reservoir valve 20e may be place in the supply line 14 to ensure the supply line remains primed.

In view of the above, the oral hydration system 10 can be used to maintain hydration or to treat dehydration in a subject by providing any of the above described hydration systems 10, filled with a hydrating fluid; and opening the proximal valve 20b to deliver fluid to an individual in need of hydration. In embodiments where the proximal valve 20b is a bite valve, the method may include opening the proximal valve 20b by biting the bite valve. Biting can deform the valve 20*b* for opening or can pressurize a proximal sub-chamber 42*b* to forcibly eject the fluid. In each configuration, preferably the distal valve 20*a* remains closed while the proximal valve 20*b* is open.

In embodiments where the hydration system 10 includes a third valve 20*c* positioned between the distal and proximal valves 20*a*, 20*b*, optionally at the proximal region of the compressible chamber 16, and where the third valve 20*c* is biased in a closed position, the method also includes opening the third valve 20*c* by the compression of the chamber 16. Furthermore, closing the proximal valve 20*b* and optionally a third valve 20*c* and releasing the chamber 16 to open the distal valve 20*b* refills the chamber under vacuum.

The invention described herein may be embodied in other specific forms without departing from the spirit or essential characteristics thereof. The specific embodiments previously described are therefore to be considered as illustrative of, and not limiting, the scope of the invention.

What is claimed is:

1. An oral hydration system that reversibly mounts to a structure and delivers fluid to a person in need of hydration at variable flow rates, the system comprising:
   a) a fluid reservoir comprising a handle formed from a bendable metal wire with a polymer coating that is configured to reversibly mount the oral hydration system to a structure by bending around the structure and remaining bent until the handle is reversibly bent to release the reservoir from the structure, wherein:
      the handle is co-molded or bonded to the reservoir, or the reservoir comprises a lid and the handle is co-molded or bonded to the lid;
   b) a supply tube fluidly coupled to the reservoir at its distal end; and
   c) a mouthpiece pump molded as a single piece and deformable along its entire length, wherein the pump is fluidly coupled at its distal end to a proximal end of the supply tube, wherein the pump or the supply tube comprises a one-way distal valve and the pump is sealed proximally with a proximal face in a form of a mouthpiece containing a valve that seals until the pump is deformed by a user.

2. The hydration system according to claim 1, wherein the reservoir comprises a lid with recessed channels for releasably attaching the supply tube.

3. The hydration system according to claim 1, wherein the reservoir, a reservoir lid, or the bendable coated wire further comprises a magnet and an opposing magnet is located in close proximity to the pump or at the proximal end of the supply tube for releasably holding the supply tube to the reservoir, the reservoir lid or the bendable coated wire respectively.

4. The hydration system according to claim 1, wherein the supply tube comprises a removable and bendable guidewire that maintains a bent shape, thereby configuring the supply tube to be adjustably bent to maintain a variety of orientations.

5. The hydration system according to claim 4, further comprising a brush adapted for reversible connection to the guidewire and sized to brush the interior of the mouthpiece and/or the supply tube.

6. An oral hydration system that reversibly mounts to a structure and delivers fluid to a person in need of hydration at variable flow rates, the system comprising:
   a) a fluid reservoir configured for reversibly mounting the hydration system to a structure;
   b) a supply tube fluidly coupled to the reservoir at its distal end, wherein the reservoir comprises a lid optionally channeled to accept the supply tube, further wherein the lid and supply tube comprise magnets for magnetic attraction, thereby providing a magnetic holding mechanism for the supply tube;
   c) a mouthpiece pump fluidly coupled to the proximal end of the supply tube, wherein the pump is molded as a single piece and deformable along its entire length, the pump comprising a first opening at its distal end for attachment to the supply tube, the pump or the supply tube further comprising a one-way distal valve and at a proximal end of the pump is a mouthpiece with a proximal valve that seals against leaking fluid until deformed by a user or compression of the pump, wherein the proximal valve of the mouthpiece sufficiently seals to prevent air induction when under a vacuum force during pump decompression.

7. The hydration system according to claim 6, wherein the distal valve is biased in an open position.

8. The hydration system according to claim 6, wherein the proximal valve is configured to open when compressing the mouthpiece to eject fluid.

9. The hydration system according to claim 6, wherein the pump comprises three valves comprising the proximal valve, the distal valve, and a third valve positioned between the distal and proximal valves, preferably at the proximal region of the pump, to form two sub-chambers of different volumes within the pump.

10. The hydration system according to claim 9, wherein the third valve is biased in a closed position and is selectively opened during compression of the pump.

11. The hydration system according to claim 9, wherein each of the three valves are biased in a closed position, wherein the proximal valve is configured to open and the distal and third valves are configured to close when compressing a proximal sub-chamber of the pump, optionally by biting or pinching, thereby releasing a volume of fluid from the proximal sub-chamber and upon decompression the proximal valve is configured to close and the distal and third valves are configured to open to permit refilling the proximal sub-chamber under vacuum.

12. The hydration system according to claim 6, further comprising an inline flow rate control valve positioned distal to the distal valve that regulates a maximum rate of fluid flow independent of compression and regulates the rate which the pump refills.

13. The hydration system according to claim 12, wherein the flow rate control valve comprises an adjustable indexed selector to select the maximum rate of flow through the flow rate control valve.

14. The hydration system according to claim 6, further comprising a safety ring positioned around an outside of the mouthpiece to limit entry of the hydration system into a mouth of an individual receiving hydration, wherein the safety ring is reversibly attachable around the mouthpiece.

15. The hydration system according to claim 6, wherein the pump is reversibly connected to the supply tube utilizing one attachment.

16. The hydration system according to claim 6, wherein the mouthpiece portion is covered with a foam sleeve.

17. A method for hydration comprising:
   a) providing the hydration system according to claim 6, filled with a hydrating fluid; and
   b) opening the proximal valve to deliver fluid to an individual in need of hydration.

18. The method according to claim 17, wherein the proximal valve is a bite valve, wherein the step of opening the proximal valve comprises biting the bite valve or compression of the pump.

19. The method according to claim 17, wherein the distal valve remains closed while the proximal valve is open.

20. The method according to claim 19, further comprising compressing the pump to increase flow of fluid through the opened proximal valve.

21. The method according to claim 20, wherein the hydration system further comprises a third valve positioned between the distal and proximal valves, optionally at the proximal region of the pump, wherein the third valve is biased in a closed position, the method further comprising opening the third valve by the compression of the pump or a suction force applied by a user.

22. The method according to claim 21, further comprising closing the proximal valve and releasing the pump to close the third valve and open the distal valve, thereby refilling the pump under vacuum.

23. The hydration system according to claim 6, further comprising a handle co-molded, bonded or reversibly attached to the lid.

24. The hydration system according to claim 6, further comprising a handle co-molded, bonded or reversibly attached to the reservoir.

25. An oral hydration system comprising:
a) a fluid reservoir;
b) a supply tube fluidly coupled to the reservoir at its distal end;
c) a reversibly compressible chamber fluidly coupled to the supply tube;
d) a mouthpiece proximate to or at a proximal end of the compressible chamber; and
e) at least two valves that regulate the flow of fluid through the hydration system, wherein a distal valve is positioned at a distal end of the chamber or along the supply tube and is biased in an open position, and a proximal valve is positioned at the mouthpiece and biased in a closed position, wherein the distal valve is configured to close in response to compression of the chamber.

26. The hydration system according to claim 25, wherein the fluid reservoir comprises a bendable mount configured to reversibly mount the oral hydration system to a structure by bending around the structure.

27. The hydration system according to claim 25, wherein the at least two valves comprise three valves, wherein a third valve is positioned between the distal and proximal valves to form two compressible sub-chambers of different volumes.

28. The hydration system according to claim 27, wherein the third valve is configured to remain closed during compression of a proximal sub-chamber.

* * * * *